US006316423B1

(12) United States Patent
Von Lubitz et al.

(10) Patent No.: US 6,316,423 B1
(45) Date of Patent: Nov. 13, 2001

(54) METHOD OF TREATING ISCHEMIC, HYPOXIC AND ANOXIC BRAIN DAMAGE

(75) Inventors: Dag K. J. E. Von Lubitz, Brighton, MI (US); Kenneth A. Jacobson, Silver Spring, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/155,931

(22) PCT Filed: Apr. 1, 1997

(86) PCT No.: PCT/US97/05399

§ 371 Date: Mar. 4, 1999

§ 102(e) Date: Mar. 4, 1999

(87) PCT Pub. No.: WO97/37667

PCT Pub. Date: Oct. 16, 1997

Related U.S. Application Data

(60) Provisional application No. 60/014,760, filed on Apr. 10, 1996, and provisional application No. 60/019,073, filed on May 9, 1996.

(51) Int. Cl.[7] .................................................. A61K 31/70
(52) U.S. Cl. ............................................................. 514/46
(58) Field of Search ................................................ 514/46

(56) References Cited

U.S. PATENT DOCUMENTS

| | | |
|---|---|---|
| 3,551,409 | 12/1970 | Kampe et al. . |
| 3,660,380 | 5/1972 | Schmidt et al. . |
| 3,932,645 | 1/1976 | Meyer et al. . |
| 4,048,171 | 9/1977 | Bossert et al. . |
| 4,213,984 | 7/1980 | Schmidt et al. . |
| 4,213,985 | 7/1980 | Schmidt et al. . |
| 4,380,547 | 4/1983 | Materne . |
| 4,381,301 | 4/1983 | Rainer . |
| 4,532,248 | 7/1985 | Franckowiak et al. . |
| 4,546,182 | 10/1985 | Kjellin et al. . |
| 4,820,709 | 4/1989 | Hofer . |
| 4,879,296 | 11/1989 | Daluge . |
| 4,925,847 | 5/1990 | Hofer . |
| 5,140,015 | 8/1992 | Olsson et al. . |
| 5,248,770 | 9/1993 | Jacobson et al. . |
| 5,284,834 | 2/1994 | Jacobson et al. . |
| 5,310,731 | 5/1994 | Olsson et al. . |
| 5,324,832 | 6/1994 | Jacobson et al. . |
| 5,443,836 | 8/1995 | Downey et al. . |
| 5,453,426 | 9/1995 | Jacobson et al. . |
| 5,502,064 | 3/1996 | Junge et al. . |
| 5,688,774 | 11/1997 | Jacobson et al. . |
| 5,773,423 | 6/1998 | Jacobson et al. . |

FOREIGN PATENT DOCUMENTS

| | | |
|---|---|---|
| 2 228 377 | 1/1974 | (DE) . |
| 2524284 | 10/1976 | (DE) . |
| 0 161 877 | 11/1985 | (EP) . |
| 0 197 488 | 4/1986 | (EP) . |
| 0 212 340 | 3/1987 | (EP) . |
| 0 217 530 | 4/1987 | (EP) . |
| 0 239 186 | 9/1987 | (EP) . |
| 0 387 070 | 9/1990 | (EP) . |
| WO 86/00310 | 1/1986 | (WO) . |
| WO 94/14832 | 7/1994 | (WO) . |

OTHER PUBLICATIONS

Ali et al., *Experimental Biology*, (1997).
Ali et al., *J. Biol. Chem.*, 265, 745–753 (1990).
Ares et al., *Abstracts of Papers of the American Chemical Society*, 209, 190–MEDI, (1995).
Beaven et al., *Trends Pharm. Sci.*, 15, 13–14 (1994).
Borea et al., *Eur. J. Pharmacol.* (Mol. Pharm. Section), 267, 55–61 (1994).
Borea et al., *Int. J. Purine and Pyrimidine Res.*, 3, 65 (1992).
Boyd et al., *Experimental Biology Abstracts*, (1996).
Brackett et al., *Biochem. Pharmacol.*, 47, 801–814 (1994).
Bruns et al., *Molecular Pharmacology*, 29, 331–346 (1986).
Bruns et al., *Proc. Natl. Acad. Sci. USA*, 77(9), 5547–5551 (1980).
Busto et al., *Journal of Cerebral Blood Flow and Metabolism*, 7, 729–738 (1987).
Cantor et al., *Journal of Neurochemistry*, 59(5), 1884–1892 (1992).
Carruthers et al, *Trends in Pharmacological Sciences*, 14 8, 290–291 (1993).
Cermak et al., *Tetrahedron Letters*, 22, 2331–2332 (1981).
*Chemical Abstracts*, vol. 106:67009K (1987).
*Chemical Abstracts*, vol. 111:77745(g) (1989).
*Chemical Abstracts*, vol. 98:1252(z) (1983).
*Chemical Abstracts*, vol. 98:125211z (1983).
Cheng et al., *Biochem. Pharmacol.*, 22, 3099–3108 (1973).
Daly et al., *Biochemical Pharmacology*, 35(15), 2467–2481 (1986).
Dudley et al., *Society for Neuroscience Abstracts*, 19, Abstract No. 42.11 (1993).
Eynde et al., *Tetrahedron*, 51, 23, 6511–6516 (1995).
Fozard et al., *Br. J. Pharmacol.*, 109, 3–5 (1993).
Fozard et al., *Br. J. Pharmacol.*, 109, 3–5 (1993).
Francis et al., *J. Med. Chem.*, 31, 1014–1020 (1988).
Gallo–Rodriguez et al., *J. Med. Chem.*, 37, 636–646 (1994).
Hide et al., *Mol. Pharmacol.*, 41, 352–359 (1992).
Hu et al., *Pharmacology and Technology*, 61, 121–125 (1987).
Ijzerman et al., *Drug Design and Discovery*, 9, 49–67 (1992).

(List continued on next page.)

Primary Examiner—Zohreh Fay

(57) ABSTRACT

The present invention provides a method of treating ischemic, hypoxic or anoxic brain damage in an animal comprising administering to an animal afflicted with ischemic, hypoxic, or anoxic brain damage, or an animal in imminent danger of suffering ischemic, hypoxic, or anoxic brain damage, a therapeutically effective amount of ADAC, or an analogue thereof.

21 Claims, 6 Drawing Sheets

OTHER PUBLICATIONS

Ismail et al., *Arzneimittel–Forschung/Drug Research*, 45, 8, 865–868 (1995).
Jacobson et al., *J. Med. Chem.*, 28(9), 1334–1340 (1985).
Jacobson et al., *J. Med. Chem.*, 35, 407–422 (1992).
Jacobson et al., *Journal of Medicinal Chemistry*, 35(22), 4143–4149 (1992).
Jacobson et al., *FEBS Letters*, 323, 141–144 (1993).
Jacobson et al., *FEBS Letters*, 336, 57–60 (1993).
Jacobson et al., *Drugs of the Future*, 20 7, 689–699 (1995).
Jacobson et al., *Neuropharmacology*, 36, 1157–1165 (1997).
Jacobson et al., *Trends Pharmacol. Sci.*, 19, 184–191 (1998).
Jarvis et al., *J. Pharmacol. Exp. Therap.*, 251, 888–893 (1989).
Jasper et al., *Biochem. Pharmacol.*, 43, 119–130 (1992).
Ji et al., *Drug Development Research*, 33, 51–59 (1994).
Ji et al., *Research Communications*, 203, 570–576 (1994).
Jiang et al., *J. Med. Chem.*, 39, 4667–4675 (1996).
Jiang et al., *J. Med. Chem.*, 40, 2596–2608 (1997).
Johnson et al., *J. Org. Chem.*, 59, 5854–5855 (1994).
Kampe et al., *Chem. Abstr.*, 70, 88212z (1969).
Kim et al., *Journal of Medicinal Chemistry*, 3373–3382 (Sep. 1994).
Kim et al., *Journal of medicinal Chemistry*, 3614–3621 (Oct. 1994).
Kim et al., *Journal of Medicinal Chemistry*, 37, 4020–4030 (1994).
Koch et al., *Chem. Abstr.*, 72, 21921c (1970).
Kusachi et al., *J. Med. Chem.*, 29, 989–996 (1986).
Linden et al., *Mol. Pharmacol.*, 44, 524–532 (1993).
Marangos, *Chemical Abstracts*, 105: 127265g (1986).
Meade, et al., *Journal of Pharmacology and Experimental Therapeutics*, 279, 5, 1148–1156 (1990).
Meyerhof et al., *FEBS Letters*, 284(2), 155–160 (Jun. 1991).
Meyerhof et al., *FEBS Letters*, 284(2), 155–160 (Jun. 1991).
Minamisawa et al., *Stroke*, 21(5), 758–764 (1990).
Mitchell et al., *Neurosurgery*, 36(5), 1003–1008 (1995).
*Molecular Pharmacology*, 29, 331–346 (1986).
Mosselhi, *Nucleos. Nucleot.*, 12, 431–439 (1993).
Mungall et al., *J. Org. Chem.*, 40, 1659–1662 (1975).
Murphy et al., *Chemical Abstracts*, 99: 187500x (1983).
Mustafa et al., *Journal of Pharmacology and Experimental Therapeutics*, 268 3, 1328–1334 (1994).
Nikodijevic et al., *FEBS Letters*, 261(1), 67–70 (Feb. 1990).
Olah et al., *Mol. Pharmacol.*, 45, 978–982 (1994).
Pfister, *Synthesis*, 8, 689–690 (1990).
Ramkumar et al., *J. Biol. Chem.*, 268, 16887–16889 (1993).
Salvatore et al., *Proc. Natl. Acad. Sci. U.S.A.*, 90, 10365–10369 (1993).
Schingnitz et al., *Nucleosides & Nucleotides*, 10(5), 1067–1076 (1991).
Schwabe et al., *Naunyn–Schmiedeberg's Arch. Pharmacol.*, 313, 179–187 (1980).
Siddiqi et al., *Nucleosides & Nucleotides*, 12, 267–278 (1993).
Siddiqi et al., *Presentation, Amer. Chem. Soc. Meeting*, Washington, D.C., (Aug. 1994).
Stiles et al., *J. Biol. Chem.*, 260, 10806–10811 (1985).
Tiwari et al., *Nucleosides & Nucleotides*, 13, 1819–1828 (1994).
Von Lubitz et al., *European Journal of Pharmacology*, 263, 59–67 (1994).
Von Lubitz et al., *European Journal of Pharmacology*, 275, 23–29 (1995).
Von Lubitz et al., *European Journal of Pharmacology*, 302, 43–48 (1996).
Von Lubitz et al., *European Journal of Pharmacology*, 316, 171–179 (1996).
Von Lubitz et al., *Neurosci. Abstr.* (1994).
Von Lubitz et al., *Society for Neuroscience Annual Meeting*, Oct. (1994).
Vorbrüggen et al., *Chem. Ber.*, 114, 1234–1255 (1981).
Welsh et al., *Journal of Cerebral Blood Flow and Metabolism*, 10, 557–563 (1990).
Yao, Y. et al., *Biochem. Biophys. Res. Comm.*, 232, 317–322 (1997).
Zhou et al., *Proc. Natl. Acad. Sci. USA*, 89, 7432–7436 (Aug. 1992).
Van Bergen et al., Abstract of American Chemical Society Meeting, Chicago, Illinois (Aug. 25, 1993).
van der Wenden et al, *Drug Devel. Res.*, 31, 314 (Abstract 1190) (1994).
Van Galen et al., *J. Med. Chem.*, 34, 1202–1206 (1991).
Van Galen et al., *Medicinal Research Reviews*, 12(5), 423–471 (1992).
Van Galen et al., *Mol. Pharmacol.*, 45, 1101–1111 (1994).
Van Galen et al., *Nucleos. Nucleot.*, 10, 1191–1193 (1991).
Van Galen et al., *Nucleosides & Nucleotides*, 9(2), 275–291 (1990).
Van Rhee et al., *Journal of Medicinal Chemistry*, 39 15, 2980–2989 (1996).
Van Rhee et al., *Journal of Medicinal Chemistry*, 39 2, 398–406 (1996).
Von Lubitz et al., *Annals of New York Academy of Sciences*, 765, 163–178 (1995).
Von Lubitz et al., *Drug Devel. Res.*, 31, 332 (Abstract 1224) (1994).
Von Lubitz et al., *European Journal of Pharmacology*, 219, 153–158 (1992).

ated in 1995, in press). However, these studies required drug doses in the milligram

METHOD OF TREATING ISCHEMIC, HYPOXIC AND ANOXIC BRAIN DAMAGE

This application claims benefit to Provisional Application No. 60/014,760 Apr. 10, 1996 and claims benefit to 60/019,073, May 9, 1996.

TECHNICAL FIELD OF THE INVENTION

The present invention relates to a method of using certain adenosine amine congeners in the prevention and treatment of brain damage caused by ischemia, hypoxia, and anoxia.

BACKGROUND OF THE INVENTION

Despite intense research aimed at the development of effective therapeutic interventions, the means of preventing post-ischemic brain damage are still elusive. Among the numerous therapies currently under testing, approaches based on the stimulation of adenosine $A_1$ receptors offer a substantial promise in reducing ischemia-related structural and functional damage (for recent reviews, see Rudolphi et al., Cerebrovasc. Brain Metab. Rev., 4, 346 (1992); Miller et al., J. Neurotrauma Suppl., 2, S563 (1992); von Lubitz et al., N.Y. Acad. Sci., 765, 163 (1995)).

Multiple studies have shown that acute stimulation of adenosine $A_1$ receptors results in decreased calcium influx, enhanced membrane hyperpolarization, suppressed release of neurotransmitters (including neurotoxic glutamate), and depression of NMDA receptor excitability (reviewed by Schubert et al., Neuroprotective mechanisms of endogenous adenosine action and pharmacological implications, in: Pharmacology of Cerebral Ischemia, ed. J. Krieglstein, H. Oberpichler (Wissenschaftliche Verlagsgesselsschaft mbH, Stuttgart), 417 (1990); Rudolphi et al., supra; von Lubitz et al., J. Mol. Neurosci., 2, 53 (1992); von Lubitz et al., Adenosine: a Drototherapeutic concept in neurodegeneration, in Neuroprotective agents: Clinical and Experimental Aspects, B. Trembly and W. Slikker, Jr., (eds.) Ann. N.Y. Acad. Sci., 765, 163 (1995a)). As a result of these effects, neuronal excitability and firing rate are reduced causing, in turn, a substantial reduction of brain metabolic demands (Schubert et al., supra).

The events elicited by stimulation of adenosine $A_1$ receptors counteract several processes recognized as key participants in the generation of ischemic brain damage (see, von Lubitz et al., 1995a, supra; Bengtsson et al., Cell damage in cerebral ischemia: *physiological, biochemical, and structural aspects*, A. Schurr and B. M. Rigor (eds) in: Cerebral Ischemia and Resuscitation (CRC Press, Boca Raton), 1990; Choi, J. Neurobiol., 9, 1261 (1992)). Hence, several successful attempts have been made to demonstrate the neuroprotective value of treatment with agonists acting at this adenosine receptor subtype (see, von Lubitz et al., 1995 supra). Although most of these studies demonstrated unequivocally that both pre- and postischemically administered adenosine $A_1$ receptor agonists reduce postischemic neuronal loss (reviews by Miller et al., supra; Rudolphi et al., supra; von Lubitz et al., 1995, supra), a paucity of data describing the effect of these drugs on postischemic neurological recovery exists (see, e.g., Phillis and O'Regan, 1988; von Lubitz et al., J. Mol. Neurosci., 2, 53 (1992), Heron et al., Brain Res., 641, 217 (1994)).

It is well known that both focal and global ischemia may result in very significant disturbances of cognitive functions in both humans (Mohr et al., Middle cerebral artery, in: Stroke, H. J. M. Barnett, J. P. Mohr, B. M. Stein, F. M. Yatsu (eds.) Churchill Livingstone, N.Y. 377 (1986); Mohr, Posterior cerebral artery, in: Stroke, H. J. M. Barnett, J. P. Mohr, B. M. Stein, F. M. Yatsu (eds.) Churchill Livingstone, N.Y.), 377 (1986)) and in animals subjected to an experimental cerebrovasculatory arrest (Bothe et al., Stroke, 17, 1160 (1985); Auer et al., Neurosci. 9, 1641 (1989); le Peillet et al., Modified open-field activity test to study the protective activity of drugs in cerebral ischemia in rats (4 vessel model), in: Pharmacology of Cerebral Ischemia (1988), J. Krieglstein (ed.) (CRC Press, Boca Raton), 369 (1989); Jaspers et al., Neurosci. Lett. 117, 149 (1990); Katoh et al., Brain Res. 577, 57 (1992)). Short term and spatial memory appears to be particularly affected (Mohr et al., 1986a, supra).

For example, cardiac arrest and cerebrovascular arrest involving either middle or posterior cerebral artery frequently result in retro- and anterograde amnesia in humans (Mohr, supra; Mohr et al., supra). Typically, all of these insults involve severe damage to the hippocampus, which is the brain region postulated to be intimately involved in learning processes related to spatial coding (O'Feefe et al., Med. Sci. Res., 16, 897 (1978)). Amnesia, determined in a wide variety of learning paradigms, has also been reported in several animal species exposed to experimentally induced loss of the hippocampal formation (Mishkin, Nature, 273, 297 (1978); Morris et al., Nature, 297, 681 (1982); Bothe et al., Supra; Hagan et al., Beh. Brain Res., 41, 151–160 (1990); Jaspers et al., supra). Moreover, in many instances of brain ischemia, treatment is not available to the patient until hours, in stroke patients typically 3 to 6 hours, after the ischemic injury. Such a delay places great demands on any therapeutic regime designed to mitigate ischemic brain injury, and to date there exists no known method for effectively treating this damage, especially following these significant delays in initiating such treatment.

Unlike treatment of ischemic brain damage, adenosine-based treatment of cardiovascular diseases has reached its clinical reality, and drugs such as Adenocard™ or Persantine™ are now available worldwide to the community of cardiologists. Yet, apart from carbamazepine, whose antagonistic properties at adenosine $A_1$ receptors are marginal, and which is used in prophylaxis of affective disorders (van Calker et al., Drug Dev. Res., 3, 354 (1993)), the treatment of neurodegenerative diseases with adenosine $A_1$ receptor active drugs is generally limited to experimental practice. While both the neuroprotective and anticonvulsant impact of acute administration of adenosine $A_1$ receptor agonists became fully recognized (reviews by Fredholm et al., TIBS, 9, 130 (1995); von Lubitz et al., Adenosine in: a protherapeutic concept in neurodegeneration, in Neuroprotective agents: Clinical and Experimental Aspects, (eds.) B. Trembly and W. Slikker, Jr., Ann. N.Y. Acad. Sci. 765, 163 (1995), Von Lubitz et al., Behavioral effects of adenosine receptor stimulation, in: Adenosine and Adenine Nucleotides: From Molecular Biology to Integrative Physiology, L. Belardinelli and A. Pelleg, (eds.) Kluwer Academic Publ., Boston, 489 (1995)). The presence of disturbing side effects, e.g., bradycardia and hypotension (Williams, Drug Dev. Res., 28, 438 (1993)) has severely mitigated introduction of these drugs as clinically viable alternatives in treatment of such disorders as stroke or seizures.

Previous studies show that preischemic treatment with adenosine $A_1$ receptor agonists results in significant improvement in neuronal survival and mortality reduction (Rudolphi et al., supra; von Lubitz et al., 1995, in press). However, these studies required drug doses in the milligram range (reviews by Rudolphi et al., supra, and von Lubitz et al., supra) which result in disturbing and clinically unacceptable cardiovascular side effects including (but not necessarily limited to) bradycardia and hypotension. Such side effects are considered the most serious obstacle in clinical development of adenosine $A_1$ receptor stimulating agents (Williams, supra).

Therefore, there exists a need for a method of preventing and treating ischemic brain damage without the aforesaid undesirable side-effects associated, for example with selective $A_1$ adenosine receptor agonists that provide neuroprotective effects. The present invention seeks to provide such a method of preventing and treating ischemic, hypoxic, or anoxic brain damage. These and other objects and advantages of the present invention, as well as additional inventive features will be apparent from the description of the invention provided herein.

SUMMARY OF THE INVENTION

The present invention provides a method of treating ischemic, hypoxic, or anoxic brain damage in an animal, particularly a human, comprising administering to an animal recently afflicted with ischemic, hypoxic, or anoxic brain damage, or an animal in imminent danger of suffering ischemic brain damage, a therapeutic dose of N6-[4 [[[[4-[[[(2-aminoethyl)amino]carbonyl]methyl]anilino ]carbonyl] methyl]phenyl]adenosine (ADAC), or structural analogues of ADAC.

BRIEF DESCRIPTION OF DRAWINGS

FIG. 3A is a cross section of the brain of a control animal, and FIG. 3B is a cross section of the brain of an ADAC-treated animal.

DESCRIPTION OF THE PREFERRED EMBODIMENTS

Figure 1:
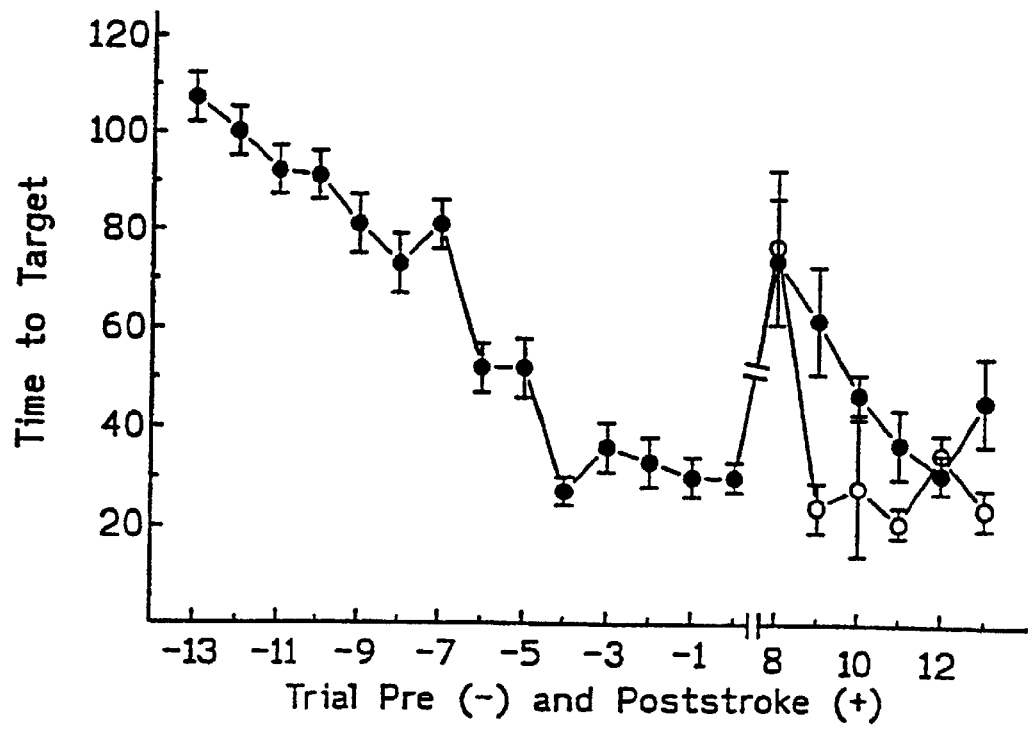
FIG. 1 depicts the "time to target" for gerbils in the Morris water maze test (mean±S.E.M.) plotted as a function of the trial day. The solid circles indicate the times to target of control animals, and the open circles indicate the times of ADAC-treated animals. Experimental ischemia is administered on day 0. ADAC is administered 15 minutes prior to ischemia.

The present invention is predicated, at least in part, on the surprising discovery that ADAC (N6-[4 [[[[4-[[[(2-aminoethyl)amino]carbonyl]methyl]anilin o]carbonyl] methyl]phenyl]adenosine) is effective for postischemic neuropreservation in the brain at concentrations at least ten-fold (10-fold) lower than 30 other $A_1$ adenosine receptor selective agonists previously studied (e.g., cyclohexyladenosine (CHA)). The present invention provides a method of treating or preventing ischemic, hypoxic, or anoxic brain damage or suffering from ischemic, hypoxic, or anoxic brain damage comprising administering to an animal at risk or suffering from such brain damage a therapeutically or prophylactically effective amount of an $A_1$ adenosine receptor selective adenosine amine congener. Administration of ADAC at 0.1 mg/kg in normoxic animals (gerbils) is not accompanied by a statistically significant bradycardia, hypotension, or decreased cerebral (cortical) blood flow within the 120 minutes following intraperitoneal injection of the drug. Moreover, at this dose, the drug does not induce behavioral changes as measured by open field locomotor activity tests. Similar to other $A_1$ adenosine receptor agonists, ADAC at higher concentrations manifests cardiovascular effects within 30 minutes of administration of 0.3 mg/kg and beyond. These properties indicate that ADAC has a similar but more potent mode of neuroprotection as other $A_1$ adenosine receptor agonists. Thus, ADAC can be of utility in the prevention of postischemic brain damage, whereas other $A_1$ adenosine receptor agonists generally are not as useful due to the serious side-effects attendant the use of these other $A_1$ adenosine receptor agonists.

The present invention is illustrated through the use of ADAC, as defined herein above, but one of skill in the art will appreciate that other amine congeners of adenosine that are closely related to ADAC can be substituted for ADAC. The suitability of such compounds for substitution is dependent upon the selectivity of these analogues for $A_1$ adenosine receptors. Example 10, infra, identifies five compounds with structures and affinities for $A_1$ adenosine receptors that are substantially similar to ADAC and can therefore be used as ADAC substitutes in the context of the present invention.

As revealed in the examples below, ADAC is very effective at preventing or attenuating postischemic brain damage. Experimental measurements of the therapeutic value of ADAC include a variety of assays, including both behavioral assays and histological analysis of brain sections of gerbils. The examples further reveal that ADAC is surprisingly effective at low dosages whether administered preischemically or postischemically. When administered postischemically it is advisable that ADAC be administered within one day of the ischemic insult. Although, neuroprotection can be effected at least as late as 14 hours after brain reperfusion (Rudolphi et al., supra) the lack of detailed studies on the "window of treatment" in mammalian systems dictates that treatment should preferably be carried out within 12 hours of ischemic alleviation (or reperfusion). More preferably, the treatment should occur within 6 hours of alleviation of ischemia. Yet more preferably, the administration of ADAC should occur within 3 hours of alleviation of ischemia. Even more preferred is that the treatment occur between 30 minutes and 2 hours after the alleviation of ischemia. Optimally, if the treatment must occur postischemically, the treatment should occur about 30 minutes from the time of reperfusion. There is no evidence, however, that postischemic administration of ADAC is preferable to preischemic administration. Unfortunately, the occurrence of potentially brain damaging ischemia is often not predictable, and, therefore, administration of ADAC will often, of necessity, be performed postischemically. In view of these issues ADAC can be administered within any suitable period of time as can be determined by a skilled clinician for each patient in need of treatment.

Currently, there are not any forms of postischemic brain damage which are not expected to benefit from therapeutic administration of ADAC. Thus, one skilled in the art will recognize that the indications that can be beneficially treated by preischemic or postischemic administration of ADAC include cerebral ischemia, stroke, neonatal hypoxia, hypoxia caused by compromised lung function, neonatal anoxia, anoxia caused by compromised lung function, cerebral trauma, secondary regional ischemia induced by brain edema, increased intracranial pressure, open brain surgery, endarterectomy, surgical interventions involving temporary, artificially sustained arrest of cardiopulmonary functions resulting in impairment of cerebral blood flow, and emergency medical treatment involving CPR. This list of indications resulting in anoxia or hypoxia of the brain is given for the sake of illustration and should not be interpreted as limiting the scope (or utility) of the invention. Further, it should be noted that there are aspects of these medical indications that are not responsive to treatment by ADAC. That is, ADAC administration is useful in the context of this invention for the treatment and attenuation of brain damage resulting from ischemia, hypoxia, and anoxia. Thus, the present invention should not be construed as indicating that ADAC is therapeutic for cancerous malignancies of the brain per se, even though ADAC administration is useful in the treatment of the brain ischemia that can result from the occurrence of brain cancer.

The ADAC and ADAC analogues useful in the context of the present inventive method can be administered to an animal, especially a mammal (e.g., a gerbil), and preferably a human, by any suitable means or routes. Such administrative means or routes include, for example, parenterally, subcutaneously, intravenously, and intraperitoneally. Preferably, the administrative means or route is chosen to maximize application of the ADAC and ADAC derivatives to the brain while minimizing the exposure of other organs to the therapeutic ADAC and ADAC derivatives. Of course, such optimized routes of administration can differ significantly between differing causes of brain ischemia. Inevitably, the optimal route of administration should be determined by a skilled clinician on the basis of the clinician's expertise and experience.

The dose administered to an animal, particularly a human, in the context of the present invention should be sufficient to cause a desirable response, e.g., diminution of neuron death, memory loss, or reorganization of the fine structure of the brain. One skilled in the art will recognize that dosage will depend upon a variety of factors including the potency of the particular adenosine congener employed, the age, species, condition, and body weight of the animal or patient, as well as the extent of the ischemia. The size of the dose will also be determined by the route, timing, and frequency of administration as well as the existence, nature, and extent of any adverse side-effects (e.g., allergic reaction) that might accompany the administration of ADAC (or an ADAC analogue) and the desired physiological effect.

The quantity of ADAC (or ADAC analogue) to be administered will be less than the amount that causes undesirable side-effects (e.g., bradycardia) in the afflicted animal. Typically, this is expected to be less than 1 mg/kg of body weight. Advantageously, this will be on the order of 0.1 mg ADAC/kg body weight. If appropriate, as determined by a skilled clinician, ADAC can be administered at concentrations as low as 0.01 to 0.001 mg/kg body weight. Of course, if the ADAC is administered in such a fashion as to concentrate its application in the affected tissues or otherwise potentiate its effect, even lower dosages may be effective. The adjustment of these dosages can be modified upward or downward by one of skill in the art as warranted by particular circumstances, although the optimal dosage range typically will be from 0.03 to 0.3 mg/kg body weight.

The present invention also provides a pharmaceutical composition comprising a pharmaceutically acceptable carrier and a therapeutically effective amount of one or more of ADAC and ADAC analogues useful in the context of the present inventive method. Any suitable carrier can be used in the pharmaceutical composition, which, of course, will depend on the particular means or route of administration, as well as other practical considerations. Such practical considerations include, but need not be limited to, providing a carrier lacking reactivity toward ADAC (or ADAC analogues), and protection of the ADAC (or ADAC analogues) from inactivation or degradation prior to delivery to neuronal tissues.

The pharmaceutically acceptable carriers described herein, for example, vehicles, excipients, or diluents, are well-known to those who are skilled in the art and are readily available to the public. Accordingly, there is a wide variety of suitable formulations of the pharmaceutical composition of the present invention. The following formulations are merely exemplary and not meant to be limiting.

Injectable formulations are among those formulations that are preferred in accordance with the present inventive methods. The requirements for effective pharmaceutical carriers for injectable compositions are well known to those of ordinary skill in the art (See *Pharmaceutics and Pharmacy Practice*, J. B. Lippincott Company, Philadelphia, Pa., Banker and Chalmers, eds., pages 238–250, (1982), and ASHP *Handbook on Injectable Drugs*, Toissel, 4th ed., pages 622–630 (1986)). It is preferred that such injectable compositions be administered intravenously or locally, i.e., at or near the ischemic brain region.

Formulations suitable for parenteral administration include aqueous and non-aqueous, isotonic sterile injection solutions, which can contain anti-oxidants, buffers, bacteriostats, and solutes that render the formulation isotonic with the blood or cerebral spinal fluid of the intended recipient, and aqueous and non-aqueous sterile suspensions that can include suspending agents, solubilizers, thickening agents, stabilizers, and preservatives. The ADAC (or ADAC analogues) may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral.

Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-$\beta$-aminopropionates, and 2-alkyl-imidazoline quaternary ammonium salts, and (e) mixtures thereof.

The parenteral formulations will typically contain from about 0.5 to about 25% by weight of ADAC (or ADAC analogue) in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injection, immediately prior to use. Extemporaneous injection solutions and suspensions can be prepared from sterile powders, granules, and tablets of the kind previously described.

Finally, care should be taken in the formulation of these vehicles such that adverse neuro-stimulants or depressants that either attenuate the potency of ADAC (or ADAC analogue) or synergistically accentuate possible side-effects of $A_1$ adenosine receptor agonists are not included.

The following examples further illustrate the present invention but, of course, should not be construed as in any way limiting its scope.

DRUG ADMINISTRATION FOR THE EXAMPLES

Adenosine amine congener N6-[4 [[[[4-[[[(2-aminoethyl) amino]carbonyl]methyl]anilino]carbonyl]methyl]phenyl] adenosine (AD dissolved in a 20:80 (v/v) mixture of Alkamus EL-620 (Rhone-Poulenc, Cranbury, N.J.) and phosphate buffered saline. The drug was administered as a single 0.15 cc intraperitoneal injection of 0.1 mg ADAC/kg body weight 15 minutes prior to ischemia or at the indicated time postischemia. Pilot studies showed that the time point of postischemic vehicle injection has no influence on the subsequent course of recovery of control animals. Therefore, control groups were given a 0.15 cc injection of the vehicle at 15 minutes postischemia when ADAC was administered postischemically.

EXAMPLE 1

This example illustrates that, contrary to other $A_1$ adenosine receptor agonists which cause significant side-effects at neuroprotective dosages, ADAC is virtually side-effect free at protective dosages.

ADAC was administered at 100$\mu$g/kg body weight to nonischemic gerbils. Such an administration did not cause any significant changes of body temperature, cardiac rate or mean arterial blood pressure (Table 1) to the nonischemic gerbils. Blood pressure was monitored using a Harvard Apparatus (South Natick, Mass.) rat tail blood pressure monitor (von Lubitz et al., 1994 supra), while a Silogic EC-60 cardiac and respiratory monitor (Stewartstown, Pa.) was used to measure cardiac rate. EEG clip electrodes were attached to the unshaven loose skin of the armpits and to both thighs saturated with EEG gel. Moreover, ADAC administration at this level did not induce any behavioral changes as determined by open field locomotor activity testing.

TABLE 1

| Cardiovascular effects of 100 $\mu$g/kg ADAC in nonischemic animals | | |
|---|---|---|
| Time | Cardiac rate (beats/min ± SEM) | Blood pressure (mm Hg ± SEM) |
| Preinjection | 384 ± 10 | 81 ± 2 |
| 5 min post | 385 ± 6 | 83 ± 1 |
| 15 min post | 382 ± 7 | 81 ± 1 |
| 30 min post | 383 ± 8 | 82 ± 2 |
| 60 min post | 383 ± 6 | 80 ± 2 |

This example establishes that ADAC administration at effective dosages does not induce the side-effects that have been primarily responsible for preventing other adenosine receptor agonists from being in the treatment of ischemic brain damage.

EXAMPLE 2

The following example illustrates the therapeutic benefit of administering ADAC preischemically as indicated by measured mortality rates.

A series of gerbils were separated into a control group (to which no ADAC was administered) and a test group (to which ADAC was administered), and then transient acute ischemia was induced in both groups of animals. Seven control animals out of 20 (35%) died during the initial 12 hour period following 10 minutes of ischemia. Three additional control gerbils died between day 1 and 3, and 2 additional animals died 5–8 hours following a water maze trial by day 14. Thus, the overall death rate of the control group was 60%. In contrast, in the ADAC-treated group only 2 animals out of 10 died (20%) during the entire monitoring period, one on day 3 and one on day 6.

This example illustrates that 0.1 mg/kg of ADAC administered preischemically a single time results in a dramatic reduction of the death rate due to transient acute ischemia and significantly delays the occurrence of the deaths it does not prevent.

EXAMPLE 3

This example illustrates that preischemic ADAC administration protects spatial memory as measured by the Morris water maze test.

The Morris water maze (Morris et al., supra) is now considered the most direct means of assessing post-ischemic memory and learning of spatially oriented tasks (Corbett et al., *Neuroreport*, 3, 204 (1992)). This test is well known in the art and the specific parameters of this test as used herein are defined below. Female gerbils (Tumblebrook Farms, Mass.) weighing 70 g were used in the study. Prior to inclusion in the experiments, animals were tested for susceptibility to spontaneous seizures using the method described by Lee et al., *Neuropharmacol.*, 5, 517 (1984). Seizure-prone gerbils were rejected.

The details of the water maze are known in the art (von Lubitz et al., 1993 supra). Briefly, the system consists of a tank (1 m diameter) which is filled with opaque water to a depth of 30 cm. The tank contains a colorless target platform (15 cm diameter) submerged to a depth of 1.5 cm and placed in the center of the north-west quadrant. Two highly contrasting spatial markers are suspended from the north and east walls of the tank facing toward its center. The starting point for each trial is the south-east wall. During trials, animal movements are tracked, preferably using a computer-assisted method such as that provided by the Watermaz data acquisition program available from Infallible Software, Research Triangle Park, N.C.

Prior to water maze trials, gerbils are acclimatized to swimming by daily immersion in water of incrementally increasing depths (i.e., 3 cm, 10 cm, 15 cm, and 30 cm). During acclimatization, all spatial clues and the target were removed from the tank and its vicinity. Since exposure to water induced spontaneous seizures in some animals, seizing gerbils were excluded from further experiments. After the final exclusions, 30 animals entered water maze training.

Pre-ischemic training consisted of three phases: the invisible target acquisition phase, the probe test, and the visible target test defined below. Global learning in the water paradigm was tested during the invisible target acquisition phase. The probe test, during which the target was removed, served to isolate and test the spatial component of the learned task. Finally, the visible target was used to investigate both visual and motor ability of animals to reach the target, and to test their motivation to perform the water maze task.

Each invisible target acquisition trial lasted 120 seconds. The acquisition trials were continued until the animals reached a stable performance plateau. Following three days of stable target acquisition times, animals were subjected to the probe trial lasting 60 seconds. The visible target trial was administered on the same day as ischemia. In order to preclude the influence of swimming stress on the post-ischemic outcome, the visible test was performed 8 hours prior to the occlusion. Additional details of the water maze testing procedure have been described previously in the art (Sei et al., *FASEB J.* 6, 3008 (1992); von Lubitz et al., *Eur. J. Pharmacol.*, 249, 271 (1993)).

Post-ischemic training was commenced after an 8-day recovery period. The training schedule followed the same pattern as that prior to the insult. Acquisition training was discontinued after control animals reached preischemic target latency. Probe trial and visible target trial were administered during the two days immediately following the post-ischemic acquisition phase.

Prior to subjecting the gerbils to 10 minutes of ischemia, the gerbils were randomly divided into the control and the drug testing groups. Previous studies indicated 50–60% post-ischemic mortality among control animals (von Lubitz et al., *Eur. J. Pharmacol.* 219, 153 (1992); von Lubitz et al. *Eur. J. Pharmacol.*, 263, 59 (1994) and, maximally, 20% among drug treated gerbils. Therefore, 20 animals were assigned to the control group and 10 to the ADAC group in order to assure an adequate number of survivors available for post-ischemic water maze testing in both groups. Bilateral carotid occlusion was performed under Halothane anesthesia as described previously (von Lubitz et al., supra). Body/brain temperature was maintained at the pre-ischemic level by means of an infrared heating lamp and a heating blanket (Such heating instruments are commonly available; the instruments used herein were supplied by Harvard Instruments, South Natick Mass.). During post-ischemic recovery, animals were monitored each day for signs of functional damage (e.g., pareses) that might affect their subsequent water maze performance. Postischemic mortality was also monitored every day.

Several studies have demonstrated that cerebral ischemia induces persistent postischemic locomotor hyperactivation (see, e.g., Philis and O'Regan, *Med. Sci. Res.*, 16, 897 (1988); Katoh et al., supra; Gao et al., *Life Sci.*, 3, PL 61–65 (1994); Mileson et al., *Neurosci. Lett.* 128, 71 (1990)). Since locomotor hyperactivation may result in a spurious improvement of performance in the water maze (von Lubitz et al., 1993, supra), open field activity of all gerbils was assessed 7 days after the occlusion (i.e., one day prior to the water maze experiments). During locomotor testing, horizontal displacement of each gerbil was monitored in 2 minute epochs for 10 minutes using a Digiscan activity monitor (available from Omnitech Electronics, Colombus, Ohio).

Locomotor activity tests performed 7 days after ischemia revealed a significant main effect of drug treatment [$F(1,8)=220.824$, $P<0.001$] with all ADAC treated animal consistently showing lower open field activity than the controls when measured over a 10 minute period (i.e., $135\pm6$ cm vs. $235\pm3$ cm). Thus, ADAC administration significantly protected against the changes in locomotor activity that are associated with ischemic brain damage.

Figure 2:
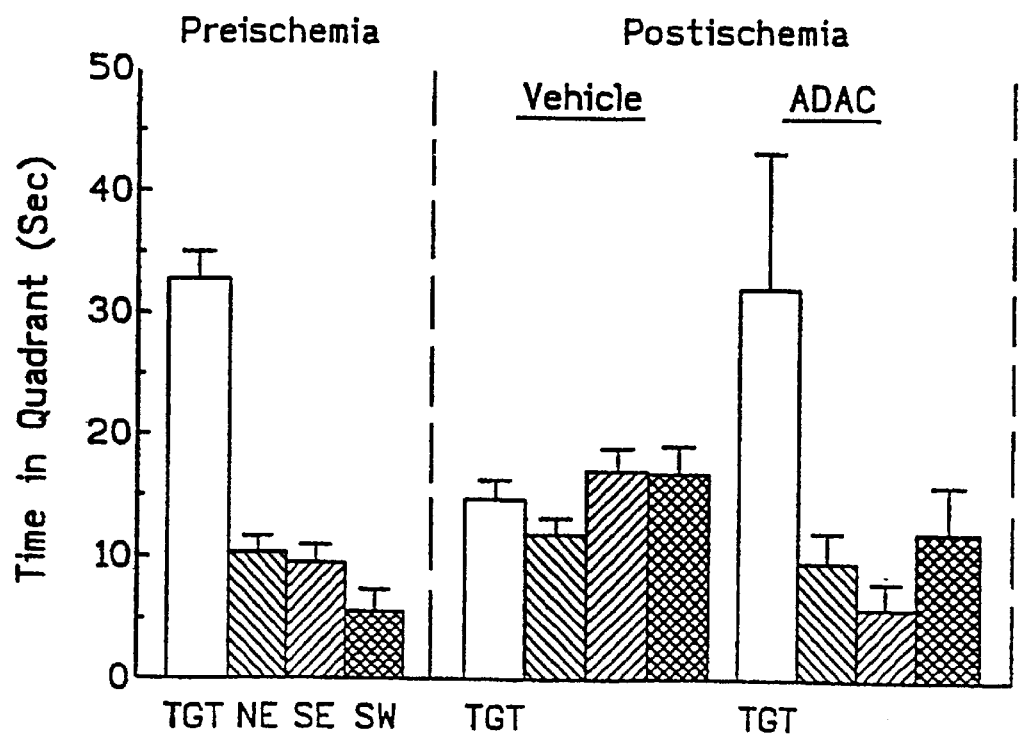
FIG. 2 depicts the gerbils preference for each quadrant of the watermaze. The left panel illustrates the gerbils times of quadrant occupancy after completing preischemic training. The right hand panel shows the gerbils times of quadrant occupancy postischemically when treated postischemia with vehicle or ADAC. Quadrant abbreviations are TGT, target quadrant; NE, northeast; SE, southeast; SW, southwest.

The gerbils were then subjected to the water maze testing. Training studies of water maze activity of all animals showed changes in search patterns (from wall-hugging (i.e., thigmotactic) to center-cross patterns) and quadrant preference developed during preischemic training. For example, the probe trial revealed a significant main effect of quadrants [$F(3,27)=35.351$, $P<0.001$) with the time spent in the target quadrant ($37.7\pm2.3$ seconds) being significantly different from that spent in the other three quadrants ($6\pm3$ to $10\pm2$ seconds). These data were then used for reference in the analysis of the effect of ADAC administration on postischemic water maze performance. The resulting data is plotted in FIG. 1, which reveals that the drug treated gerbils (open circles) regained water maze performance levels that mirrored the plateau level obtained in preischemic training almost immediately (trial 2, day 9), whereas control animals (solid circles) required a significant degree of re-training to return to optimal levels for the control group. Significantly, the optimal performance levels for the control group approach but do not reach the optimal levels displayed by the ADAC-treated group. Further, probe trials administered postischemically revealed that while the ADAC-treated gerbils retained a high preference for the target quadrant, the control animals lost all preference for the target quadrant (i.e., the control animals spent approximately equal time in all four quadrants), as illustrated in FIG. 2.

Thus, this example shows that preischemic ADAC administration at physiologically tolerable levels results in a significant protection of spatial memory (which is thought to be particularly sensitive to brain ischemia).

EXAMPLE 4

This example illustrates the histological effects of preischemic administration of ADAC.

The gerbils of Example 3 were subjected to examination procedures subsequent to the water maze tests described in Example 3. One day after the last postischemic water maze trial, all animals were heavily anesthetized with Nembutal and perfused through the aorta with buffered (pH 7.4) formaldehyde. Frozen sections of the brains were made as described previously (Lin et al., supra). The sections were stained using the method of Nissl, and the extent of the neuronal loss was determined in the cortex, hippocampal CA1 sector, and striatum following the published protocol of von Lubitz et al. (von Lubitz, 1992, supra; von Lubitz, 1994, supra).

Figure 3A:
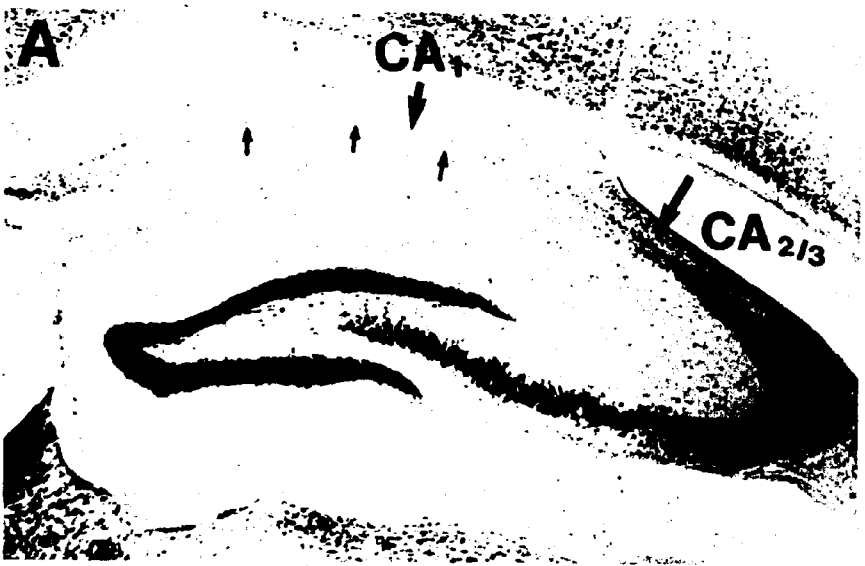
FIGS. 3A and 3B illustrate the results of hippocampal CA1 sector and striatum after Nissl staining analysis (following the protocol of von Lubitz, 1992).
Figure 3B:
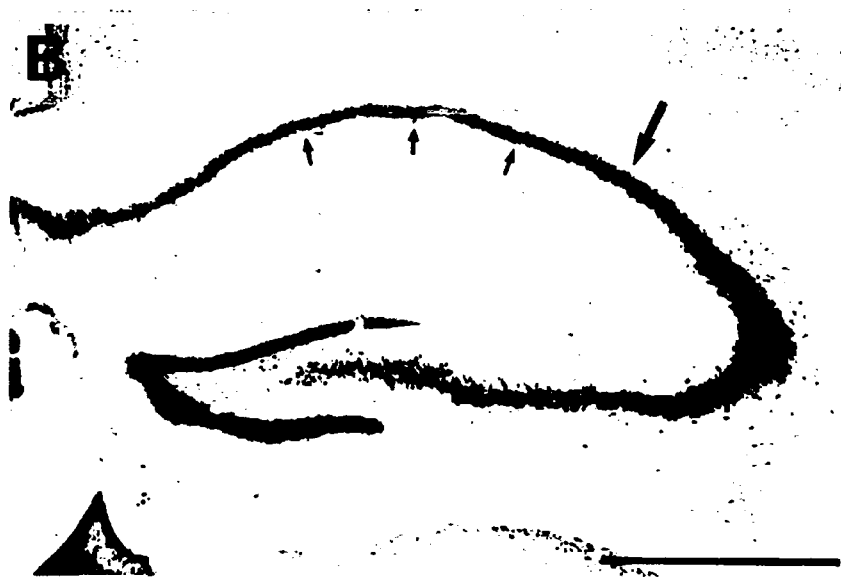

Dunnett's test, well known in the art, was used to analyze histological data. Two weeks after ischemia, very severe damage was present in the hippocampal CA1 region (see FIG. 3A) of the control animals with only 23% of the neurons surviving. These control animals also had severe damage in the cortex and dorsolateral striatum with only 83% and 25%, respectively, of the neurons surviving. In contrast, preischemic treatment with ADAC resulted in a very significant reduction of the hippocampal damage with 81% of the neurons surviving and a complete elimination of neuronal loss form both the cortex and striatum (FIG. 3).

EXAMPLE 5

This example illustrates the neuron-preserving effect of ADAC administered postischemically is significant at time points from 15 minutes to 12 hours postischemia and that, surprisingly, the effect is maximized when ADAC is administered 1 hour postischemia.

Figure 4:
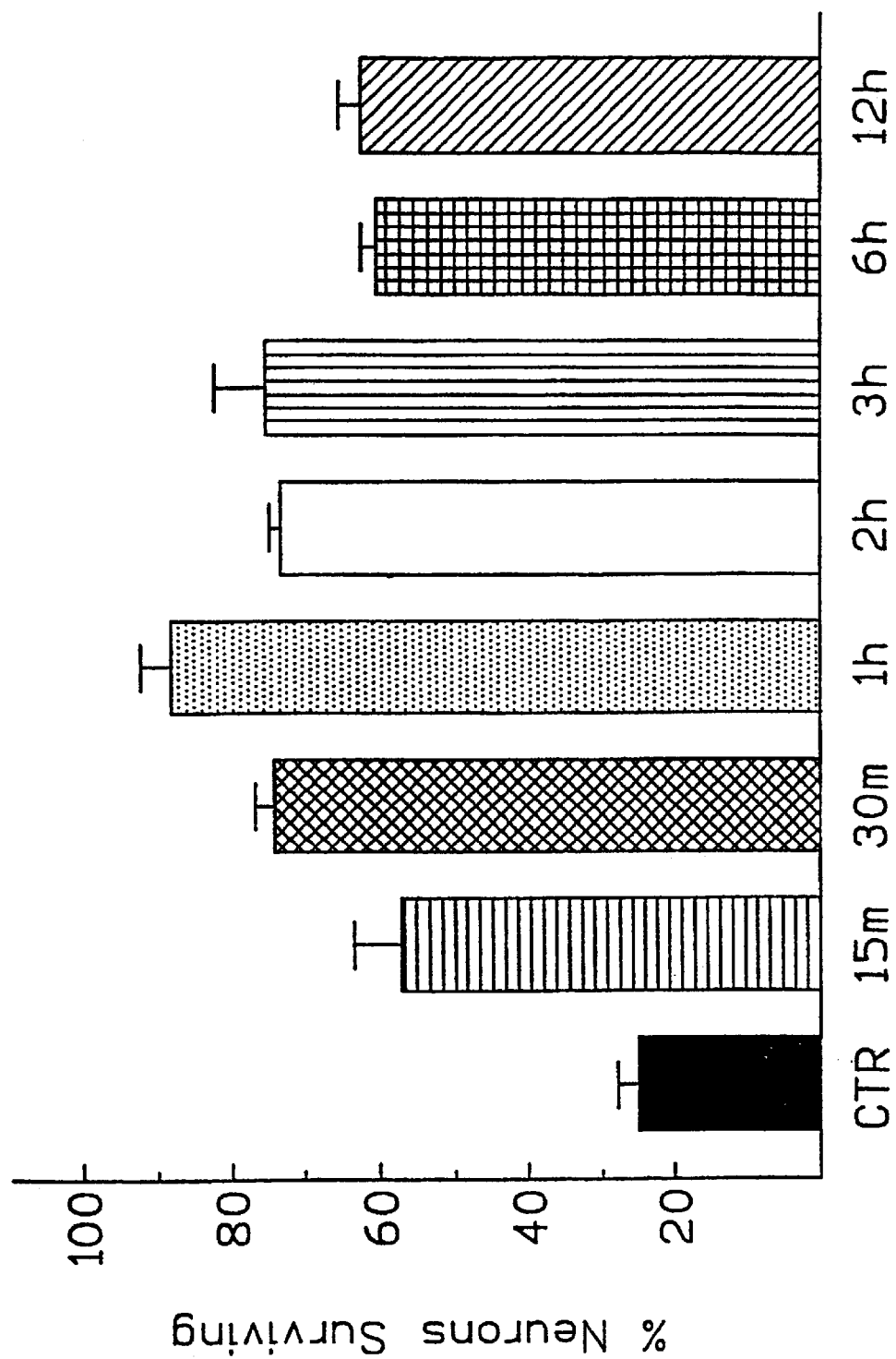
FIG. 4 depicts percentage of neurons surviving 14 days after experiencing 10 minutes of ischemia plotted as a function of postischemic time of ADAC-administration.

Neuronal survival 14 days after 10 minute ischemia is shown in FIG. 4. Increased duration of the occlusion resulted in a corresponding expansion of neuronal CA1 damage in the control group (only 25±3% neurons still present). Postischemic treatment with ADAC resulted in a statistically significant ($P<0.05$) improvement of neuronal population in the CA1 region in all treatment groups. Administration of ADAC at 1 hour postischemia produced the best results (88±4% neurons still intact in FIG. 4). Treatment at 0.5, 2 or 3 hours resulted in a similar degree of neuronal preservation among these groups (~75%, no statistically significant differences among groups). Although injection of ADAC at either 15 minutes, or at 6 or 12 hours postischemia significantly improved neuronal survival when compared to control animals ($P<0.05$), the neuron sparing effect was significantly poorer (approximately 60% neurons surviving) than when the drug was given at any other time (i.e., 0.5, 1, 2, or 3 h postocclusion). Thus, ADAC administered postischemically is also of high therapeutic value in the prevention of ischemic brain damage.

EXAMPLE 6

This example illustrates the protection of cytoskeletal structure by the administration of ADAC at varied timepoints postischemically.

Breakdown of cytoskeletal proteins such as MAP-2 has been described as one of the earliest stages of postischemic neurodegeneration (Matesic et al., *J. Neurochem*. 63, 1012 (1994)). In fact, learning impairment (at least in the gerbil model of chronic hypotension) is associated with the degradation of cytoskeletal proteins rather than neuronal loss per se (Kudo et al., *Stroke*, 21, 1205 (1990). Therefore, one plausible theory is that the memory sparing effects of either pre- or postischemic treatment with ADAC can best be ascribed to the preservation of MAP-2 (i.e., $A_1$ adenosine receptor stimulation results in preservation of MAP-2 and that this preservation is the primary reason that $A_1$ adenosine receptor stimulation is neuroprotective). Thus, the ability of ADAC to preserve MAP-2 suggests that ADAC treatment addresses the fundamental causes of memory loss and neurodegeneration that follows brain ischemia.

At the end of the survival monitoring period (14 days), control and drug treated survivors were heavily anesthetized with Nembutal (60 mg/kg, intraperitoneally), and perfused with phosphate buffered (pH 7.4) 3.5% formaldehyde as described previously (Lin et al., *Neurosci*., 2, 289 (1990). The sections were stained with the method of Nissl, and the extent of the neuronal loss in the hippocampal region was investigated according to a standard procedure as disclosed in the art (von Lubitz et al., (1992) supra; 1994)supra.

The fate of microtubule associated protein 2 (MAP-2) was determined in additional groups of animals (N=10/group) injected with 100 μg/kg ADAC at 2, 6, and 12 h following 10 minute occlusion of the carotid arteries. Animals were allowed to survive either 2 or 7 days. They were then perfused with a freshly made 3.5 solution of paraformaldehyde in phosphate buffered saline (pH 7.4). After removal, brains were cut at 40 μm, and the sections were stained immunohistochemically with a monoclonal MAP-2 antibody (Sigma) diluted 1:500–1000. Standard peroxidase antiperoxidase procedure of ABC complex with Vector kit (Hsu et al., 1981) intensified with heavy metal (Adams, 1981) was used. For immunofluorescent studies, the sections were incubated at 4° C. with the primary antibody overnight. Following three 5–10 minute washes, the sections were exposed to the secondary antibodies, i.e., fluorescein isothiocyanate, rhodamine isothiocyanate, and Texas Red conjugated goat anti-mouse IgG. The secondary antibodies were diluted at 1:20–100 in 0.1M phosphate buffer. Qualitative morphological and immunostaining characteristics of the sections were studied using an epifluorescent microscope (Nikon Labophot) equipped with filters (Nikon B2 and Nikon G1B) appropriate for the detection of the secondary antibodies.

Quantitative analysis of MAP-2 presence in the dendritic fields of CA1 was made using a computer image analysis system (Biographics Inc., Winston-Salem, N.C.).

Figure 5:
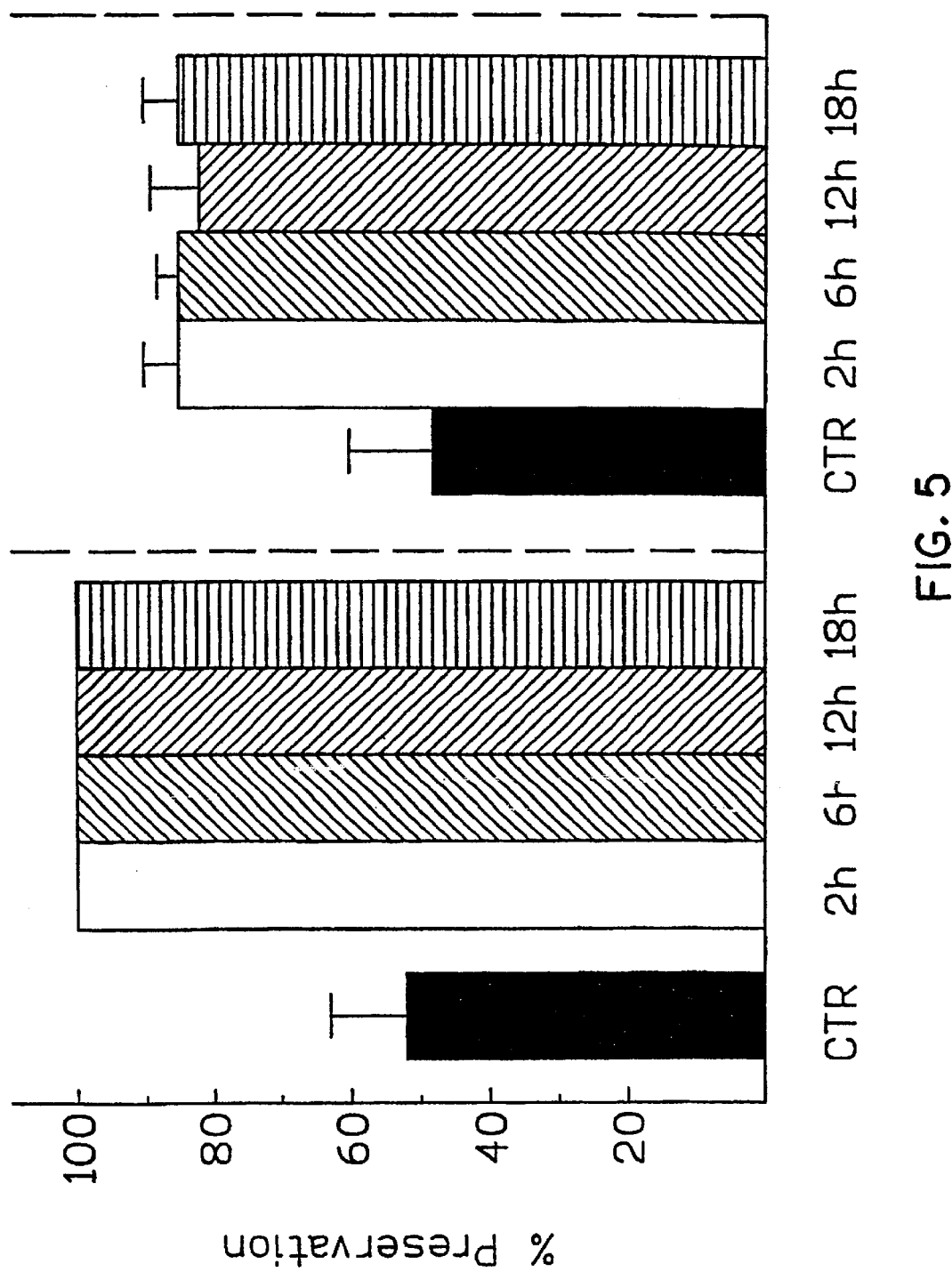
FIG. 5 depicts the degree of MAP-2 cytoskeletal protein preservation following 10 minutes of ischemia plotted as a function of the postischemic time of administration of ADAC. As above, times listed indicate the time between ischemia and ADAC administration. CTR indicates control (i.e., no ADAC administered). The left panel depicts results measured 2 days postischemia. The right panel depicts results measured 7 days postischemia.

While in the CA1 sector of control animals there was a 50% loss of MAP-2 density already 2 days after 10 minutes of ischemia (FIG. 5, left panel), there was no loss in animals treated with ADAC at 2, 6 or 12 h postischemia. Five days later (i.e., 7 days after the occlusion), MAP-2 degeneration in control animals did not progress any further(FIG. 5, right panel). In the treated groups, however, the density of MAP-2 decreased by approximately 15%.

EXAMPLE 7

The following example illustrates the improvement in survival rates of gerbils when the ADAC is administered up to 12 hours after 10 minutes of ischemia.

Groups of gerbils were given 0.1 mg ADAC/kg body weight at various times following 10 minutes of ischemia. As indicated in Table 2, only 30% of the control gerbils exposed to 10 minutes of ischemia survived until the end of the 14 day monitoring period. Statistically significant ($P<0.05$) of survival was evident in groups injected with ADAC at 15 minutes (70% survival), 30 minutes (90%), 1 hour (90%), and 2 hours (80%). In the three remaining treatment groups (i.e., 3, 6, and 12 hours) numerical improvement was apparent, but statistical significance of ($P<0.05$) was lost probably owing to the sample sizes. Survival rates in these groups were between 50% and 60% and, in part, reflect that many mortalities occur within the initial 5–6 hours postischemia, in the absence of ADAC administration. Therefore, many animals in the 6 and 12 hour treatment groups died before ADAC could be administered to them. To prevent selection of overly robust animals into these groups, the data were not normalized to account for pre-treatment mortalities. This example shows that administration of ADAC postischemically is effective at reducing mortality rates at least 12 hours postischemically and is optimally applied between 0.5 and 2 hours postischemically in gerbils recovering from 10 minutes of global ischemia.

TABLE 2

Enhancement of survival rates following ten minutes of ischemia as a function of time of postischemic ADAC administration.

| Time | Survival Rate | |
|---|---|---|
| | 24 h postischemia | 14 days postischemia |
| control | 50% | 20% |
| 15 min post | 100 | 70 |
| 30 min post | 100 | 90 |
| 1 hour post | 80 | 80 |
| 2 hour post | 80 | 80 |
| 3 hour post | 60 | 50 |
| 6 hour post | 50 | 50 |
| 12 hour post | 60 | 50 |

EXAMPLE 8

This example illustrates the dose-response parameters of ADAC administration to gerbils to prevent mortality after 10 minutes of brain-ischemia.

Figure 6:
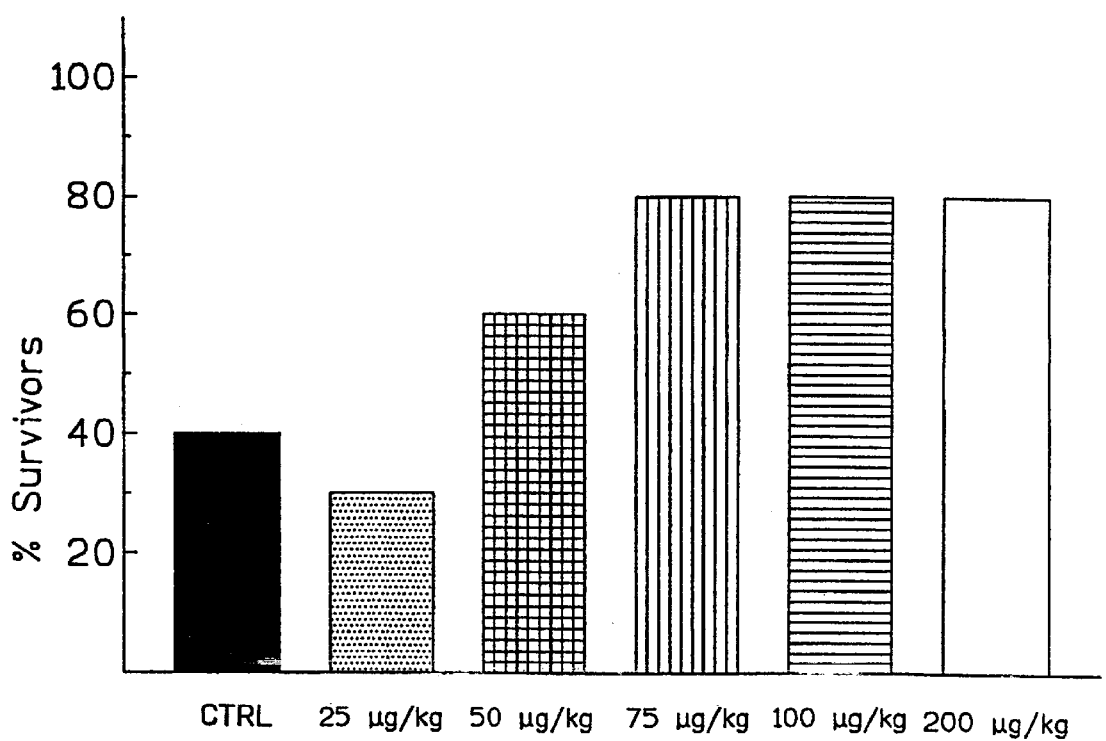
FIG. 6 depicts the survival rate of gerbils (as a percentage) exposed to 10 minutes of brain ischemia as a function of the quantity of ADAC administered 15 minutes preischemia.

Fifteen minutes before applying bilateral carotid artery occlusion varying dosages of ADAC were administered to the gerbils (FIG. 6). In the control animals (no ADAC administered) the survival rate was 40%. In the experimental groups, there was no increase in survival rate when ADAC was administered at 0.025 mg/kg body weight(30% survivors), and a moderate increase in survival rate when the drug was administered at 0.050 mg/kg body weight (60% survivors). When ADAC was administered at 75, 100, or 200 mg/kg body weight, survival rate reached a plateau at 80%. This example illustrates that ADAC is maximally and significantly effective at treating brain ischemia in gerbils at about 0.1 mg/kg body weight. This level of efficacy is about an order of magnitude better than that of other $A_1$ adenosine receptor agonists examined thus far. While not being bound to any particular theory, these data suggest that the clinical applicability (i.e., the absence of unacceptable side-effects) results from a higher selectivity for $A_1$ adenosine receptors. This higher selectivity results in lower quantities of drug administration required for maximum neuroprotection. Lower administered quantities in turn, result in attenuation or elimination of side-effects. Thus, these data indicate that ADAC is suitable for the treatment of brain ischemia in mammals, whereas other studied $A_1$ adenosine receptor agonists are not suitable.

EXAMPLE 9

This example illustrates the utility of ADAC in indications requiring prophylaxis rather than remedial treatment.

It is known in the art that long term administration of other adenosine-based $A_1$ adenosine receptor agonists can result in severe side-effects, including death. Other agonists administered at neuroprotective dosages however, are accompanied by severe side-effects not attendant the administration of ADAC at therapeutic dosages. While not being bound by any particular theory, this may explain the surprising result, detailed below, that prophylactic administration of ADAC is beneficial to animals that will be exposed to (or are likely to be exposed to) ischemia in the future, but at an unpredictable time.

Figure 7A:
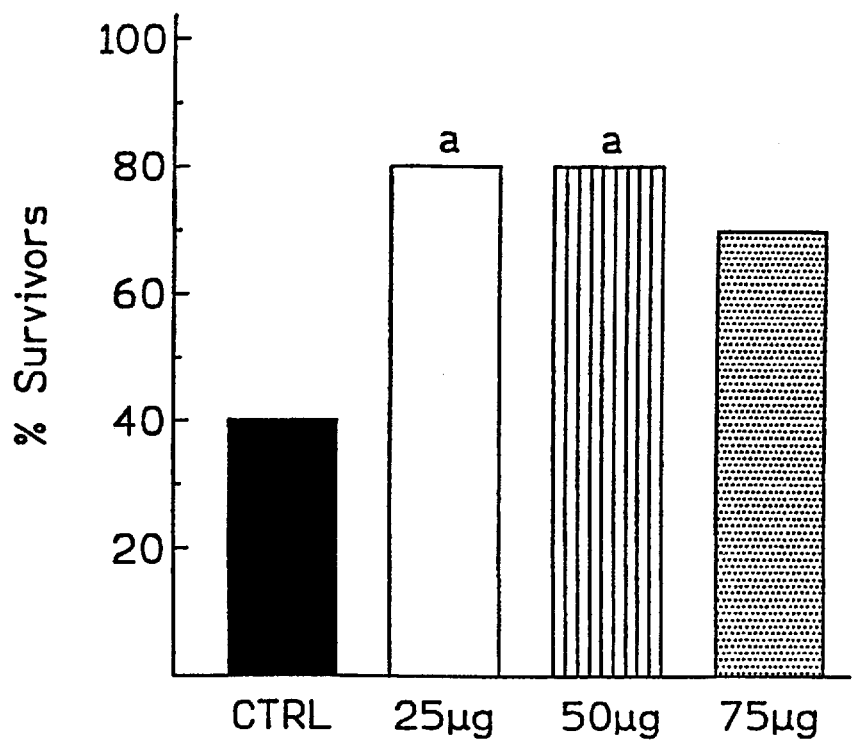
FIG. 7A depicts the survival rate of gerbils (as a percentage) exposed to chronic ADAC treatment followed by ischemia as a function of the dosage of ADAC given.
Figure 7B:
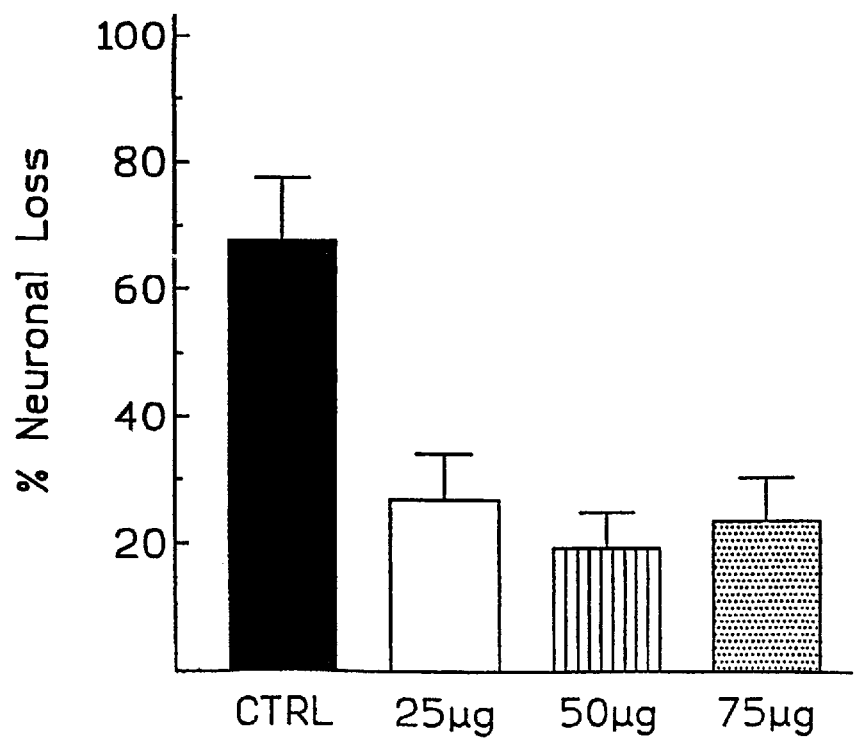
FIG. 7B depicts the loss of neurons in gerbils (as a percentage) exposed to chronic ADAC treatment followed by ischemia as a function of the dosage of ADAC given.

Gerbils (70 g females) were administered vehicle, 0.025 mg, 0.050 mg, or 0.075 mg of ADAC for 60 days, followed by one day of rest (i.e., no drug administration). The gerbils were then subjected to 10 minutes of brain ischemia and allowed to recover. Surprisingly, the chronic administration of ADAC at each of these dosages attenuated the effects of brain ischemia when measured both by survival rate (FIG. 7A) and by histological analysis of neuronal loss (FIG. 7B). Thus, this example illustrates that ADAC administration can be both safe and effective in long term prophylactic use.

EXAMPLE 10

This example illustrates the preferential selectivity of ADAC for Rat $A_1$ adenosine receptor compared to Rat $A_2$ adenosine receptor. It also defines the affinity of ADAC and ADAC-analogues for the Rat $A_1$ adenosine receptor and thereby defines by example, some suitable substitutions for ADAC.

The affinities of ADAC and five ADAC-analogues for $A_1$ adenosine receptors isolated from rats (and $A_2$ adenosine receptor for ADAC) were determined by methods known in the art. Table 3 below indicates the structure and $K_i$ values for these compounds. Thus, each of these compounds is expected to find utility in the context of the present invention. The five analogues indicated within Table 3 are given for the purposes of illustrating the nature of ADAC-analogues and is not meant to be comprehensive. Additionally, these compounds can be synthesized using a similar approach as the one employed for ADAC. These methods are known in the art. For example, the synthesis of these compounds can be guided by U.S. Pat. No. 5,248,770 or by Jacobson et al., *Journal of Medicinal Chemistry*, 28, 1341–1346 (1985).

TABLE 3

Affinities of ADAC and ADAC-analogues for $A_1$ adenosine receptors isolated from rats (and $A_2$ adenosine receptor for ADAC).

| $A_1$-AGONISTS | $K_i$: for Rat $A_1$ Receptors (nM) | $K_i$: for Rat $A_2$ Receptors (nM) |
|---|---|---|
| 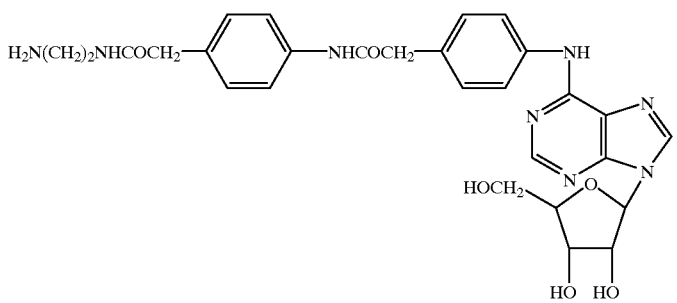 | 0.85 | 210 |

TABLE 3-continued

Affinities of ADAC and ADAC-analogues for $A_1$ adenosine receptors isolated from rats (and $A_2$ adenosine receptor for ADAC).

| $A_1$-AGONISTS | $K_i$: for Rat $A_1$ Receptors (nM) | $K_i$: for Rat $A_2$ Receptors (nM) |
|---|---|---|
| H₂N(CH₂)₃NHCOCH₂—⟨phenyl⟩—NHCOCH₂—⟨phenyl⟩—NH-adenosine | 1.96 ± 0.06 | — |
| H₂N(CH₂)₄NHCOCH₂—⟨phenyl⟩—NHCOCH₂—⟨phenyl⟩—NH-adenosine | 1.91 ± 0.17 | — |
| H₃C—⟨phenyl⟩—CONH(CH₂)ₙNHCOCH₂—⟨phenyl⟩—NHCOCH₂—⟨phenyl⟩—NH-adenosine | 11.9 ± 2.0<br>5.67 ± 0.055<br>7.95 ± 0.76 | —<br>—<br>— |

4. n = 2
5. n = 3
6. n = 4

ADAC = adenosine amine congener

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of treating ischemic, hypoxic, or anoxic brain damage in an animal at risk for ischemic, hypoxic, or anoxic brain damage or suffering from ischemic brain damage comprising administering to said animal a therapeutically or prophylactically effective amount of an $A_1$ adenosine receptor selective adenosine congener selected from the group consisting of $N^6$-phenyladenosines and pharmaceutically acceptable salts thereof.

2. A method of treating ischemic, hypoxic, or anoxic brain damage in an animal at risk for ischemic, hypoxic, or anoxic brain damage or suffering from ischemic brain damage comprising administering to said animal a therapeutically or prophylactically effective amount of an $A_1$ adenosine receptor selective adenosine congener selected from the group consisting of

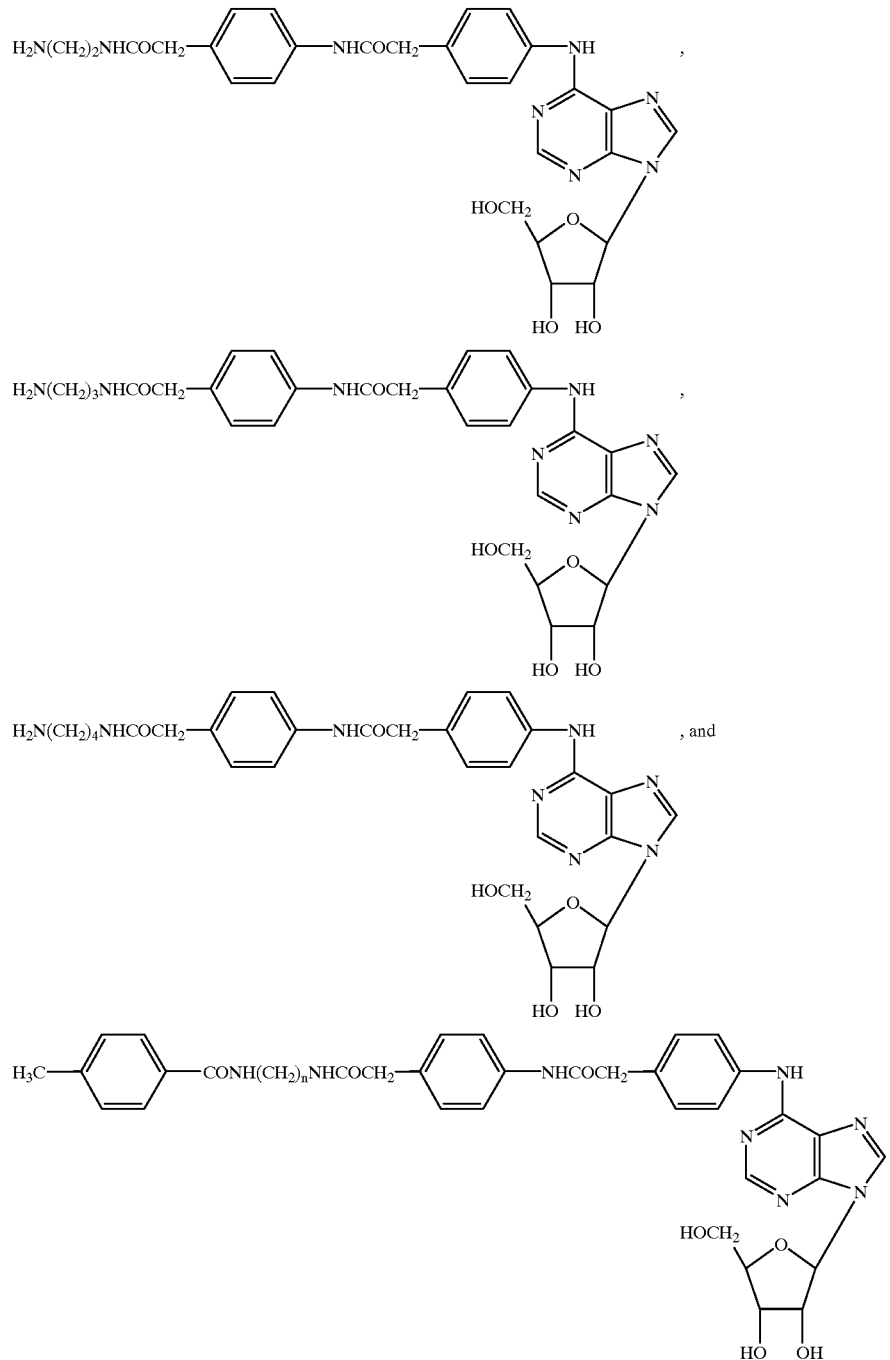

wherein n is 2, 3, or 4, and pharmaceutically acceptable salts thereof.

3. The method of claim 2, wherein said adenosine congener is N6-[4 [[[[4-[[[(2-aminoethyl)amino]carbonyl] methyl]anilino]carbonyl]methyl]phenyl]adenosine.

4. The method of claim 1, wherein the adenosine congener is administered in a pharmaceutically acceptable carrier.

5. The method of claim 1, wherein the adenosine congener is administered prior to the onset of ischemic, hypoxic, or anoxic brain damage.

6. The method of claim 1, wherein the adenosine congener is administered during an ischemic, hypoxic, or anoxic insult.

7. The method of claim 1, wherein the adenosine congener is administered after the alleviation of the brain damaging ischemia, hypoxia, or anoxia.

8. The method of claim 7, wherein the adenosine congener is administered up to 12 hours, after the alleviation of brain damaging ischemia, hypoxia, or anoxia.

9. The method of claim 7, wherein the adenosine congener is administered up to 3 hours after the alleviation of ischemic, hypoxic, or anoxic brain damage.

10. The method of claim 7, wherein the adenosine congener is administered up to 15 minutes after the alleviation of ischemic, hypoxic, or anoxic brain damage.

11. The method of claim 1, wherein said animal is a human.

12. The method of claim 1, wherein the ischemic, hypoxic, or anoxic brain damage is a result of a medical indication selected from the group consisting of cerebral ischemia, stroke, neonatal hypoxia, hypoxia caused by compromised lung function, neonatal anoxia, anoxia caused by compromised lung function, cerebral trauma, secondary regional ischemia induced by brain edema, increased intracranial pressure, open brain surgery, endarterectomy, surgical interventions involving temporary, artificially sustained arrest of cardiopulmonary functions resulting in impairment of cerebral blood flow, and emergency medical treatment involving cardiopulmonary resuscitation.

13. The method of claim 1, wherein the ischemia, hypoxia, or anoxia is a result of stroke.

14. The method of claim 13, wherein the ischemia, hypoxia, or anoxia is a result of artificially sustained arrest of cardiopulmonary functions resulting in impairment of cerebral blood flow.

15. The method of claim 2, wherein the adenosine congener is administered in a pharmaceutically acceptable carrier.

16. The method of claim 2, wherein the adenosine congener is administeredprior to the onset of ischemic, hypoxic, or anoxic brain damage.

17. The method of claim 2, wherein the adenosine congener is administered during an ischemic, hypoxic, or anoxic insult.

18. The method of claim 2, wherein the adenosine congener is administered after the alleviation of the brain damaging ischemia, hypoxia, or anoxia.

19. The method of claim 2, wherein said animal is a human.

20. The method of claim 2, wherein the ischemic, hypoxic, or anoxic brain damage is a result of a medical indication selected from the group consisting of cerebral ischemia, stroke, neonatal hypoxia, hypoxia caused by compromised lung function, neonatal anoxia, anoxia caused by compromised lung function, cerebral trauma, secondary regional ischemia induced by brain edema, increased intracranial pressure, open brain surgery, endarterectomy, surgical interventions involving temporary, artificially sustained arrest of cardiopulmonary functions resulting in impairment of cerebral blood flow, and emergency medical treatment involving cardiopulmonary resuscitation.

21. The method of claim 2, wherein the ischemia, hypoxia, or anoxia is a result of stroke.

* * * * *